US010980716B2

(12) United States Patent
Desale et al.

(10) Patent No.: US 10,980,716 B2
(45) Date of Patent: Apr. 20, 2021

(54) RELATING TO HAIR COMPOSITIONS

(71) Applicant: Conopco, Inc., Englewood Cliffs, NJ (US)

(72) Inventors: Shirish Subhash Desale, Chinchwad (IN); Christopher John Roberts, Wirral (GB); Attaporn Somboon, Bangkok (TH); Hannah Mary Southey, Great Sutton (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/763,646

(22) PCT Filed: Sep. 27, 2016

(86) PCT No.: PCT/EP2016/072924
§ 371 (c)(1),
(2) Date: Mar. 27, 2018

(87) PCT Pub. No.: WO2017/060121
PCT Pub. Date: Apr. 13, 2017

(65) Prior Publication Data
US 2018/0280260 A1    Oct. 4, 2018

(30) Foreign Application Priority Data
Oct. 7, 2015    (EP) .................... 15188753

(51) Int. Cl.
*A61K 8/00*    (2006.01)
*A61K 8/04*    (2006.01)
*A61Q 5/00*    (2006.01)
*A61Q 5/12*    (2006.01)

(52) U.S. Cl.
CPC .......... *A61K 8/046* (2013.01); *A61Q 5/00* (2013.01); *A61Q 5/12* (2013.01); *A61K 2800/30* (2013.01)

(58) Field of Classification Search
None
See application file for complete search history.

(56) References Cited

U.S. PATENT DOCUMENTS

| 1,331,518 A | 2/1920 | Mohr | |
| 3,801,015 A * | 4/1974 | Hayes | A47L 11/34 239/175 |
| 5,089,252 A * | 2/1992 | Grollier | A61K 8/8147 424/47 |
| 7,040,507 B2 | 5/2006 | Koike et al. | |
| 2007/0248736 A1 | 10/2007 | Masuda et al. | |
| 2008/0152610 A1 | 6/2008 | Cajan et al. | |
| 2014/0093468 A1 | 4/2014 | Knappe et al. | |

FOREIGN PATENT DOCUMENTS

| CN | 1356889 | 7/2002 |
| CN | 1897914 | 1/2007 |
| CN | 103764517 | 8/2012 |
| CN | 104095792 | 7/2014 |
| CN | 108136221 | 6/2018 |
| EP | 1342465 | 9/2003 |
| EP | 1792600 | 6/2007 |
| EP | 2062562 | 5/2009 |
| EP | 2625965 | 8/2013 |
| EP | 3359260 | 1/2020 |
| GB | 1331518 | 9/1973 |
| JP | 2003261430 | 9/2003 |
| JP | 2014513695 | 6/2014 |
| WO | WO9611162 | 4/1996 |
| WO | WO0076461 | 12/2000 |
| WO | WO2006007924 | 1/2006 |
| WO | WO2011116227 | 9/2011 |
| WO | WO2012154918 | 11/2012 |
| WO | WO2013014139 | 1/2013 |
| WO | WO201416354 | 1/2014 |
| WO | WO2014016351 | 1/2014 |
| WO | WO2014016352 | 1/2014 |
| WO | WO2014016353 | 3/2014 |

OTHER PUBLICATIONS

All Whipped Up Conditioning Mousse; Mintel GNPD; 2015; pp. 1-3 Record ID 3265691.
IPRP in PCTEP2016072924, dated Jan. 17, 2018.
Search Report & Written Opinion in EP15188753, dated Feb. 11, 2016.
Search Report and Written Opinion in PCTEP2016072924, dated Nov. 2, 2016.

* cited by examiner

*Primary Examiner* — Susan T Tran
(74) *Attorney, Agent, or Firm* — Foley & Lardner LLP

(57) ABSTRACT

A process for making a foamed composition, comprising the steps of a. providing a liquid hair treatment composition, b. providing a foaming device comprising a chamber, a removable or rechargeable pressurised gas unit and a dispensing nozzle, c. placing the liquid hair treatment composition in the chamber of the foamin device, d. charging the chamber with the gas, e. mixing the liquid hair treatment composition with the gas, and f. operating said foaming device such that the composition is ejected from the nozzle as a foam, wherein the liquid hair treatment composition comprises at least one conditioning ingredient and is free from hair styling polymer.

11 Claims, No Drawings

RELATING TO HAIR COMPOSITIONS

FIELD OF THE INVENTION

This invention relates to a non-aerosol method of making foamed compositions for the treatment of hair, to the foamed compositions obtainable thereby and to a method of use thereof.

BACKGROUND

Many hair products are liquids (including herein soft-solids), which are normally packaged into bottles, sachets or jars. Hair conditioner products may be rinse-off conditioners or leave-in, where product is left on the hair for an extended period of time.

Application to hair is normally carried out by dispensing onto the hand, for example by squeezing from a bottle or scooping out of a jar and then transferring onto the hair from the hand. Such application leads to a number of disadvantages. It can lead to microbial contamination by repeating scooping from the jar. The products are not homogeneously distributed onto the hair surface. Wastage occurs as liquid product can run off wet hair onto skin or shower floor.

Foamed products for application to hair are known, particularly in the styling sector, where styling mousses are a popular product format. Foam leave-on conditioners, delivered from an aerosol are also known.

WO 13/014139 (Kao) discloses a post-foaming aqueous hair styling gel composition comprising one or more thickening polymer, one or more film forming polymer, one or more polyol, one or more surfactant and one or more C4-C5 isoalkane, which is foamed after release from its packaging and applied to hair to improve shine and curl retention of hair, reduce flyaway and confer moderately good setting effect. These benefits are attributed to improved homogeneity of application to the hair. Use of the entire purchased product is said to eliminate contamination problems. A pressurised product for treating hair is also disclosed, which comprises two chambers wherein one of the chambers comprises the post foaming aqueous gel composition and the other chamber comprises one or more propellant wherein the pressure inside the vessel does not exceed 12 bar. Two chambered aerosol cans, pressurised with liquid nitrogen or carbon dioxide are exemplified.

US 2014/093468 (Henkel) Discloses a cosmetic agent for the temporary shaping of keratinic fibers, comprising a carrier, a) 0.1 to 15 wt. % of monoesters of optionally alkylated sugars with $C_6$-$C_{30}$ fatty acids, b) 0.1 to 15 wt. % of diesters of optionally alkylated sugars with $C_6$-$C_{30}$ fatty acids, c) 0 to 50 wt. % of at least one film-forming polymer, and d) 0 to 50 wt. % of at least one wax with a melting point in a range from 40° C. to 90° C., with the proviso that the proportion of component(s) c) and d) in the cosmetic agent is 0.2 to 50 wt. %. The cosmetic agent is also disclosed in the form of a foam, which has a density below 0.9 g/cm. Methods for producing the cosmetic agent by mixing an optionally premixed blend of the ingredients of the cosmetic agent, characterized in that the density of the resulting cosmetic agent is at least 10% below the density of the blend; and for the temporary shaping of hair, comprising: pressurizing the cosmetic agent with a gas, and applying the agent to the hair, are also disclosed.

EP 1792600 and US 2008/152610 (Kao) Disclose an aerosol foam wax composition with superior hair styling and conditioning effects and unusual foam appearance. Disclosed is an aqueous aerosol foam composition for keratin fibres especially for hair characterised in that it comprises at least one hair styling polymer selected from anionic, non-ionic, cationic and/or amphoteric or zwitterionic ones, at least one oil or oily compound, at least one fatty acid soap, at least one emulsifier and at least one propellant.

Despite the prior art there remains a need to deliver non-styling, pre-packaged hair products to give improved efficacy and effectiveness, without the use of propellants (due to regulatory pressure and growing consumer preference).

We have now found that liquid compositions, including packaged compositions, that comprise at least one conditioning agent and that are free from hair styling polymer, may be transformed into foams, using a non-aerosol method, said foams giving unexpected improvement in conditioning and style benefits, including increased conditioning feel, shine, smoothness, fibre alignment, volume and shape benefit over the non-foamed composition, compared with the same composition that was not foamed. The invention may be applied to a wide range of formulations.

DEFINITION OF THE INVENTION

In a first aspect, the invention provides a process for making the foamed composition of the first aspect, comprising the steps of
 a. providing a liquid hair treatment composition,
 b. providing a foaming device comprising a chamber, a removable or rechargeable pressurised gas unit and a dispensing nozzle,
 c. placing the liquid hair treatment composition in the chamber of the foaming device,
 d. charging the chamber with the gas,
 e. mixing the liquid hair treatment composition with the gas,
 f. operating said foaming device such that the composition is ejected from the nozzle as a foam,
wherein the liquid hair treatment composition comprises at least one conditioning ingredient and is free from hair styling polymer.

In a second aspect, the invention provides a foamed composition for the treatment of hair, obtainable from the method of the first aspect.

A third aspect of the invention provides a method of treating hair comprising the step of applying the foamed composition of the first aspect or as prepared by the first aspect, to hair.

DETAILED DESCRIPTION OF THE INVENTION

The Liquid Hair Treatment Composition

The term liquid, as used herein, is intended to include soft solid compositions, for example those that may be scooped out of a jar.

The liquid hair treatment composition for use in the method of the invention is capable of holding bubbles of gas in order to form a foam that is stable. It may comprise a polymer or structuring agent to enable a stable foam to be produced. In the context of the invention, by stable is meant that the foam lasts for at least sufficient time following production, to be used by the consumer in a hair treatment process.

Preferably, the liquid hair treatment composition is a packaged formulation.

The liquid hair treatment composition is preferably selected from a shampoo, a rinse-off hair conditioner, a hair mask, a leave-on conditioner composition, and a pre-treatment composition, more preferably selected from a rinse-off hair conditioner, a hair mask, a leave-on conditioner composition, and a pre-treatment composition, for example an oil treatment, and most preferably selected from a rinse-off hair conditioner, a hair mask and a leave-on conditioner composition.

Preferably, where the liquid hair treatment composition is a shampoo, it is not a high foaming shampoo.

The composition does not contain corrosive or reactive ingredients. Reactive ingredients include hair dyes, for example. Corrosive ingredients include bleach and peroxides, for example. Corrosive ingredients may cause corrosion of the chamber.

Rinse off conditioners for use in the invention are conditioners that are typically left on wet hair for 1 to 2 minutes before being rinsed off.

Hair masks for use in the present invention are treatments that are typically left on the hair for 3 to 10 minutes, preferably from 3 to 5 minutes, more preferably 4 to 5 minutes, before being rinsed off.

Leave-on conditioners for use in the invention are typically applied to the hair and left on the hair for more than 10 minutes and preferably are applied to the hair after washing and not rinsed out until the next wash.

Where the liquid hair treatment composition is a rinse-off hair conditioner, a hair mask or a leave-on conditioner composition, it suitably has a viscosity of from 5,000 to 750,000 centipoise, preferably from 50,000 to 600,000 centipoise, more preferably from 50,000 to 450,000 as measured at 30° C. on a Brookfield RVT using a Spindle A or B at 0.5 rpm for 60 seconds on a Helipath stand.

Preferably, leave-on conditioner compositions for use in the invention have a viscosity of from 50,000 to 250,000 centipoise; preferred hair masks have a viscosity of 150,000 to 600,000 centipoise and preferred rinse off conditioners have a viscosity of from 150,000 to 400,000 centipoise as measured at 30° C. on a Brookfield RVT using a Spindle A or B at 0.5 rpm for 60 seconds on a Helipath stand.

Where the liquid hair treatment composition is a shampoo, or other isotropic product, it suitably has a viscosity of from 5,000 to 100,000, preferably from 10,000 to 75,000, more preferably from 20,000 to 50,000 centipoise, as measured at 30° C. on a Brookfield RV5 at 20 rpm for 60 seconds.

The liquid composition is not a hair styling gel, a hair styling mousse, a hair styling serum or a hairspray.

Free from Hair Styling Polymer

In the context of the invention, by free from hair styling polymer is meant that the composition comprises less than 0.5 wt %, by weight of the total composition, preferably less than 0.1 wt %, more preferably less than 0.05 wt % and most preferably less than 0.01 wt % of hair styling polymer.

Hair styling polymers are polymers or resins that provide elements of style to hair, such as hold, general shape definition, shape retention, defined straightening, curling and so on, typically included in gels, mousses, serums, and hair sprays.

Some styling polymers are classed as film-forming polymers, which are often the source of "hold" in styling products such as hair gels and hairsprays. These polymers deposit onto the surface of the hair and then dry to form clear films that are strong and hold the hairs together until the film is either removed via washing or the film is broken due to mechanical forces on the hair (combing).

Examples include PVP (poly N-vinyl-2-pyrrolidone), PVA (polyvinyl acetate) and PVP/VA copolymer, amongst others.

Other styling polymers used in soft styling products, such as mousses are acrylate based, such as polyacrylates (for example polyacrylate-32, polyacylate-14), acrylates crosspolymers (for example acrylates crosspolymer-3, polyacrylate-2 crosspolymer) and AMO-acrylates/allyl methacrylate copolymer, amongst others.

Further examples of styling polymers include polyquaternium compounds, polyvinyl caprolactam copolymers and esters of PVM/MA (methyl vinyl ether and maleic anhydride).

The at Least One Conditioning Ingredient

Compositions for use in the method of the current invention comprise conditioning agents. Conditioning agents are preferably selected from cationic surfactants, used singly or in admixture.

Cationic surfactants useful in compositions for use in the method of the invention contain amino or quaternary ammonium hydrophilic moieties which are positively charged when dissolved in aqueous composition.

Examples of suitable cationic surfactants are those corresponding to the formula:

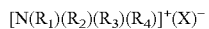

$[N(R_1)(R_2)(R_3)(R_4)]^+(X)^-$ in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions for use in the method of the present invention are monoalkyl quarternary ammonium compounds in which the akyl chain lengthy is $C_8$ to $C_{14}$.

Suitable examples of such materials correspond to the formula:

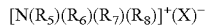

$[N(R_5)(R_6)(R_7)(R_8)]^+(X)^-$ in which $R_5$ is a hydrocarbon chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl chains (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of $C_8$ to $C_{12}$ hydrocarbyl chains.

Typical monoalkyl quarternary ammonium compounds of the above general formula for use in compositions for use in the method of the invention include:
(i) Lauryl trimethylammonium chloride (available commercially as Arquad C35 ex Akzo); cocodimethyl benzyl ammonium chloride (available commercially as Arquad DMCB-80 ex-Akzo)
(ii) Compounds of the formula:

$$[N(R_1)(R_2)((CH_2CH_2O)_xH)((CH_2CH_2O)_yH]^+(X)^-$$

wherein:
x+y is an integer from 2 to 20;
$R_1$ is a hydrocarbyl chain having 8 to 14, preferably 12 to 14, most preferably 12 carbon atoms and containing ether, ester, amido or amino moieties present as substituent's or as linkages in the radical chain;
$R_2$ is a $C_1$-$C_3$ alkyl group or benzyl group, preferably methyl, and
X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB12 ex-Akzo Nobel); PEG-5 cocomonium methosulphate (available commercially as Rewoquat CPEM ex Rewo); PEG-15 cocomonium chloride (available commercially as Ethoquad C/25 ex-Akzo).

(iii) Compounds of the formula:

$$[N(R_1)(R_2)(R_3)((CH_2)_nOH)]^+(X)^-$$

wherein:
n is an integer from 1 to 4, preferably 2;
$R_1$ is a hydrocarbyl chain having 8 to 14, preferably 12 to 14, most preferably 12 carbon atoms;
$R_2$ and $R_3$ are independently selected from $C_1$-$C_3$ alkyl groups, and are preferably methyl, and
X- is a salt-forming anion such as those selected from halogen, (e.g. chloride, bromide), acetate, citrate, lactate, glycolate, phosphate nitrate, sulphate, alkylsulphate radicals. Suitable examples are lauryldimethylhydroxyethylammonium chloride (available commercially as Prapagen HY ex-Clariant).

Mixtures of any of the foregoing cationic surfactants compounds may also be suitable. Examples of suitable cationic surfactants for use in hair compositions for use in the method of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further, suitable cationic surfactants include those materials having the CTFA designations Quaternium-5, Quaternium-31 and Quaternium-18. Mixtures of any of the foregoing materials may also be suitable. A particularly useful cationic surfactant is cetyltrimethylammonium chloride, available commercially, for example as DEHYQUART, ex Henkel.

The level of cationic surfactant is preferably from 0.01 to 10, more preferably 0.05 to 5, most preferably 0.1 to 2 w.t. % of the total composition.

A preferred conditioner comprises a conditioning gel phase. Such conditioners and methods for making them are described in WO2014/016354, WO2014/016353, WO2012/016352 and WO2014/016351.

The conditioning compositions may also comprise other optional ingredients. Such ingredients include, but are not limited to; fatty material, deposition polymers and further conditioning agents.

Conditioner compositions preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Further conditioning ingredients include esters of fatty alcohol and fatty acids, such as cetyl palmitate.

A conditioning composition for use in the present invention may preferably comprise a miscellar structured liquid.

The pH of a conditioner comprising the present composition is preferably 3-5. More preferably the pH of the composition is 4.5-5.5.

Where the composition has a pH of less than 3.10 it is preferred that it is in the form of a conditioning mask for intense treatment.

Further conditioning ingredients include conditioning oils, preferably selected from coconut oil and olive oil.

The Foamed Composition

The foamed composition is not produced by aerosolisation. The foamed composition is produced without the use of propellant.

Preferably, the foamed composition has a physical appearance similar to that of whipped cream. The colour of the foam will vary according to the colour of the original liquid composition.

The chamber is only intended to provide temporary storage for the foamed composition.

The foamed composition is used fresh, preferably within 24 hours, more preferably within 8 hours, even more preferably within 1 hour. Most preferably, the composition is foamed at point of use.

Preferably, the foamed composition is not stored in the chamber for longer than 24 hours, more preferably for more than 8 hours, most preferably more than 1 hour.

Thus, a method of the invention comprises the step of applying the foamed composition of the invention to hair. Preferably, the foamed composition is used within 24 hours of being produced, more preferably within 8 hours, even more preferably within 1 hour, most preferably within 10 minutes.

The Foaming Device

The foaming device for use in the method of the invention comprises a chamber, a removable or rechargeable pressurised gas unit and a dispensing nozzle.

It is preferably a portable, hand held device.

The Chamber

The chamber preferably has a capacity of 0.5 to 1.0 litres. It is preferably made from metal, for example stainless steel.

The Nozzle

The dispensing nozzle is for the purpose of dispensing the foamed composition.

Preferably, the nozzle is detachable. Preferably, the nozzle is operated by a lever. The nozzle may be shaped so as to result in a foamed product having a particular shape.

The Removable or Rechargeable Pressurised Gas Unit

The foamed composition is produced by the use of pressurised gas from a removable or rechargeable pressurised gas unit. Suitable examples of removable or rechargeable pressurised gas units include a gas canister and a gas cylinder. Preferably it is a gas canister, more preferably a mini gas canister, preferably of length 6 to 15 cm, more preferably less than 10 cm. The capacity of the preferred mini canisters is suitably from 10 to 100 ml.

The gas is preferably selected from carbon dioxide and nitrous oxide.

The gas is introduced into the chamber from the pressurised gas unit. The pressurised gas unit is preferably directly attachable to the device.

A preferred foaming device comprises a chamber which is detachably connected to a head, preferably by a screw thread. The head houses a connection port for a gas supply unit, a nozzle and a lever. The gas supply unit is connected to the head at the connection port to supply gas to the inside of the chamber. In use, the device is first opened by removing the head from the chamber and the liquid composition is added to the chamber. The head is then re-connected to the chamber. A gas supply is connected to the connection port on the head and gas is then injected into the chamber. A foam is generated by mixing the liquid composition and the gas, preferably by shaking. The foamed composition is then dispensed via the nozzle, preferably by operation of the lever.

The gas is pressurised gas and, therefore, cannot be atmospheric air, for example.

The Method

The process of the invention comprises the steps of
a. providing a liquid hair treatment composition,
b. providing a foaming device comprising a chamber, a removable or rechargeable pressurised gas unit and a dispensing nozzle,
c. placing the liquid hair treatment composition in the chamber of the foaming device,
d. charging the chamber with the gas,
e. mixing the liquid hair treatment composition with the gas,
f. operating said foaming device such that the composition is ejected from the nozzle as a foam, wherein the liquid hair treatment composition comprises at least one conditioning ingredient and is free from hair styling polymer.

Mixing of the liquid hair treatment composition and the gas is preferably achieved by shaking the device to mix the composition and the gas. Preferably, an essentially vertical shaking motion is carried out for 10 to 30 s.

EXAMPLES

A commercially available packaged hair mask was obtained, Nutritive (Humecterss) Mask, by Nexxus. It contained cetyl palmitate as conditioning agent and no hair styling polymer.

A commercially available food whipper, namely an "iSi Gourmet Whip", of 0.5 L capacity, fitted with a carbon dioxide mini pressurised gas canister, was used to whip the mask into a foam. First, the liquid mask composition was placed in the chamber of the foaming device, before charging the chamber with the gas. The whipper was shaken and the lever depressed to emit a foamed product.

Three mannequin heads with bleached human hair were provided. For each head, the hair was parted down the middle and each side washed with a non-conditioning shampoo, following an identical protocol.

16 g of the mask, in liquid form, was applied to one side of the mannequin head. 16 g of the foamed mask was applied to the other side. The conditioner was left on the hair for 5 minutes and then rinsed off with water.

Smoothness, shine and alignment of the hair on each side were then assessed by ten panellists, who chose the highest scoring side for each attribute. Thus, a score of 10 indicates that all ten panellists scored that side higher for that attribute.

The results are given in Tables 1-3 below.

TABLE 1

Smoothness, shine and alignment of hair treated with non-foamed (standard) mask and foamed mask.

| Head 1 | Standard Mask | Foamed Mask |
| --- | --- | --- |
| Smoothness | 0 | 10 |
| Shine | 0 | 10 |
| Alignment | 0 | 10 |

TABLE 2

Smoothness, shine and alignment of hair treated with non-foamed (standard) mask and foamed mask.

| Head 1 | Standard Mask | Foamed Mask |
| --- | --- | --- |
| Smoothness | 0 | 10 |
| Shine | 0 | 10 |
| Alignment | 0 | 10 |

TABLE 3

Smoothness, shine and alignment of hair treated with
non-foamed (standard) mask and foamed mask.

| Head 1 | Standard Mask | Foamed Mask |
|---|---|---|
| Smoothness | 0 | 10 |
| Shine | 0 | 10 |
| Alignment | 0 | 10 |

It will be seen that the hair that, in all cases, was treated with the foamed product was smoother, shinier and better aligned compared to the hair treated with the non-foamed product.

A further mannequin head, treated in the same way with the foamed product was also deemed to be visibly more controlled with added volume, have more natural movement and to look and feel less coated.

The invention claimed is:

1. A process for making a foamed composition, comprising the steps of
   a. providing a liquid hair treatment composition,
   b. providing a foaming device comprising a chamber, a removable or rechargeable pressurised gas unit and a dispensing nozzle,
   c. placing the liquid hair treatment composition in the chamber of the foaming device,
   d. charging the chamber with the gas,
   e. mixing the liquid hair treatment composition with the gas, and
   f. operating said foaming device such that the composition is ejected from the nozzle as a foam,
   wherein the liquid hair treatment composition comprises at least one conditioning ingredient and comprises less than 0.01 wt % of hair styling polymer, and
   wherein the liquid hair treatment composition is selected from a rinse-off hair conditioner, a hair mask or a leave-on conditioner composition having a viscosity of from 5,000 to 750,000 centipoise, as measured by 30° C. on a Brookfield RVT using a Spindle A or B at 0.5 rpm for 60 seconds on a Helipath stand.

2. A process as claimed in claim 1, wherein the removable or rechargeable pressurised gas unit is selected from the group consisting of a gas canister and a gas cylinder.

3. A process as claimed in claim 1, wherein the gas is selected from the group consisting of carbon dioxide and nitrous oxide.

4. A process as claimed in claim 1, wherein the liquid hair treatment composition is packaged.

5. A process as claimed in claim 1, wherein the conditioning ingredient is selected from the group consisting of a cationic surfactant, a silicone, a fatty material and an oil.

6. A foamed composition for the treatment of hair, obtainable from the process defined in claim 1, comprising at least one conditioning ingredient, wherein the composition is free from hair styling polymer.

7. A method of treating hair comprising the step of applying the foamed composition produced by the process of claim 1 to hair.

8. A method as claimed in claim 7, wherein the foamed composition is used within 24 hours of being produced.

9. The method as claimed in claim 7, wherein the method provides a benefit selected from the group consisting of improved conditioning, style benefits, increased conditioning feel, shine, smoothness, fibre alignment, volume and shape benefit to hair.

10. A process as claimed in claim 1, wherein the hair styling polymer comprises a polyquaternium compound.

11. The process as claimed in claim 1, wherein the liquid hair treatment composition is selected from a rinse-off hair conditioner, a hair mask or a leave-on conditioner composition having a viscosity of from 50,000 to 600,000 centipoise.

* * * * *